United States Patent [19]

Mueller

[11] Patent Number: 5,246,008
[45] Date of Patent: Sep. 21, 1993

[54] METHOD FOR MONITORING A PATIENT FOR REJECTION REACTIONS TO AN IMPLANTED HEART

[75] Inventor: Johannes Mueller, Berlin, Fed. Rep. of Germany

[73] Assignee: Guido Fehling, Fed. Rep. of Germany

[21] Appl. No.: 817,489

[22] Filed: Jan. 7, 1992

[30] Foreign Application Priority Data

Jan. 11, 1991 [DE] Fed. Rep. of Germany ....... 4100568

[51] Int. Cl.⁵ ............................................. A61B 5/02
[52] U.S. Cl. ............................. 128/695; 128/734
[58] Field of Search ............... 128/734, 693, 741, 774, 128/419 R, 419 N, 898, 899, 630, 903, 904, 668, 695, 696, 697, 639, 642, 644, 783, 784, 785, 799

[56] References Cited

U.S. PATENT DOCUMENTS

| 4,184,486 | 1/1980 | Papa ................................ 128/642 |
| 4,630,615 | 12/1986 | Yomtov ............................ 128/734 |
| 4,733,670 | 3/1988 | Hays et al. ........................ 128/693 |
| 4,870,967 | 10/1989 | Heinze et al. ................. 128/419 PG |
| 4,901,725 | 2/1990 | Nappholz et al. ............. 128/419 PG |
| 4,905,705 | 3/1990 | Kizakevich et al. ............... 128/696 |
| 4,915,110 | 4/1990 | Kitov ............................... 128/783 |
| 5,052,392 | 10/1991 | Schullmeyer et al. ............. 128/642 |
| 5,058,583 | 10/1991 | Geddes et al. ................ 128/419 D |
| 5,086,781 | 2/1992 | Bookspan ......................... 128/734 |
| 5,139,028 | 8/1992 | Steinhaus et al. ................. 128/697 |

FOREIGN PATENT DOCUMENTS 391798 11/1990 Austria .
2000124 8/1969 France ............................ 128/734

OTHER PUBLICATIONS

Kayser et al. "Identification of Conductive Tissue of Heart" American Journal of Medical Electronics, Jun. 1963, pp. 120-124.

Primary Examiner—Stephen C. Pellegrino
Assistant Examiner—Guy V. Tucker
Attorney, Agent, or Firm—Mason, Fenwick & Lawrence

[57] ABSTRACT

A method for monitoring a patient for rejection reactions to an implanted organ is provided with an implantable telemetry measuring unit with electrodes that can be implanted in the organ. An electric current is passed through the body tissue via two current electrodes. The impedance of the body tissue through which this current is flowing is determined with two measuring electrodes. Each of the measuring electrodes annularly surrounds one and only one current electrode. The electrodes are embedded in a support element such that they project from this support element only with their front end.

6 Claims, 2 Drawing Sheets

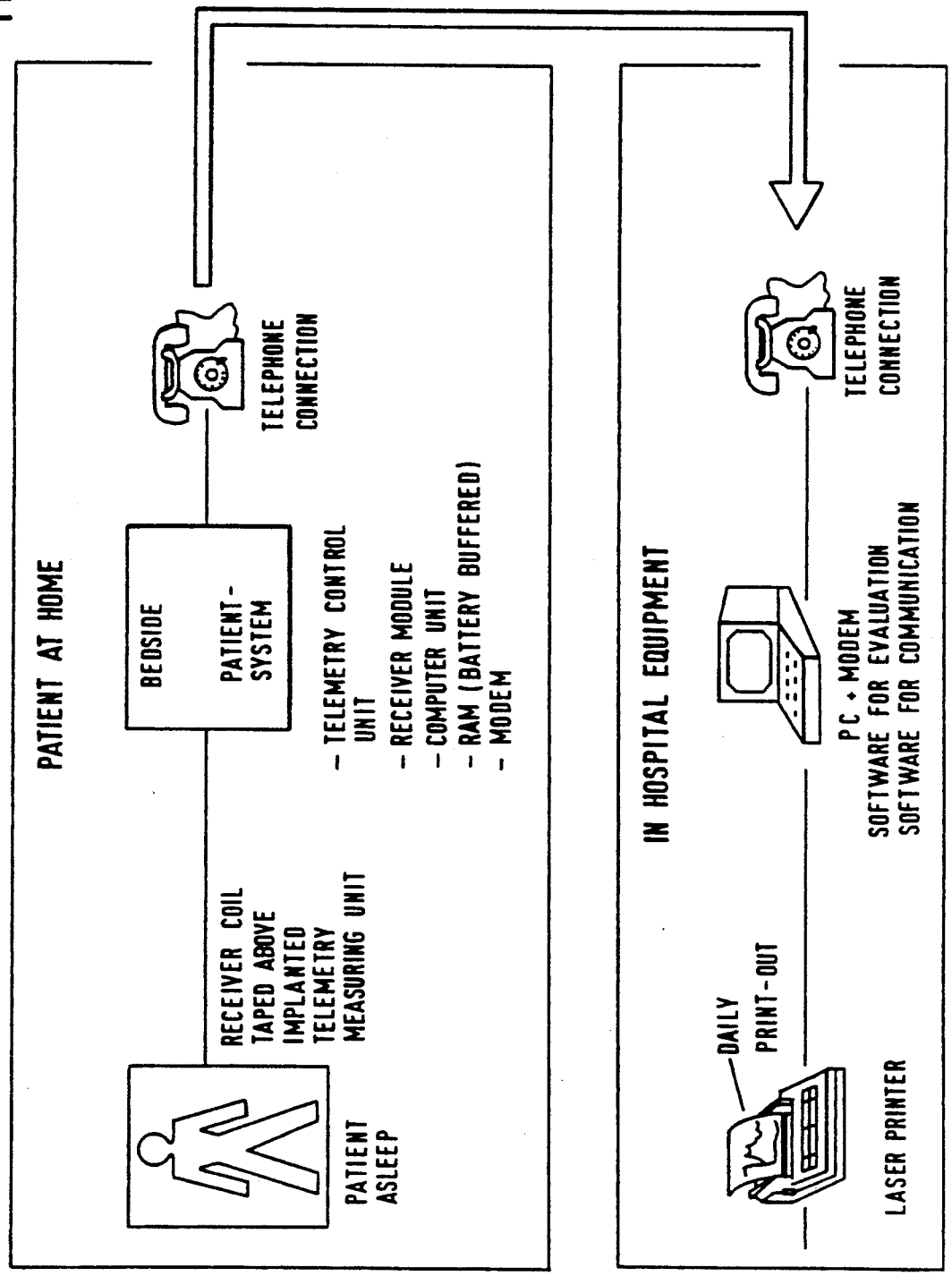

METHOD FOR MONITORING A PATIENT FOR REJECTION REACTIONS TO AN IMPLANTED HEART

BACKGROUND OF THE INVENTION

The invention relates to a method and apparatus for monitoring a patient for rejection reactions to an implanted organ, especially to an implanted heart.

Rejection of the transplanted organ, especially of a transplanted heart, represents a substantial problem in transplant medicine. Thus it is important to diagnose an incipient rejection reaction as early as possible, in order to be able to institute timely immunosuppressive therapy.

In addition to invasive endomyocardial biopsy and noninvasive echocardiography, an electrophysiological diagnostic procedure is also known in which the intramyocardial electrogram is measured by means of implanted electrodes. Preferably an implantable telemetry pacemaker, which transmits the measured values via an inductive coupling to an extracorporeal instruments (such as disclosed in U.S. Pat. Nos. 4,809,697; 4,585,004; 4,237,900; 4,550,370; 4,281,664), is used as the measuring unit in this procedure. This diagnostic procedure permits continuous monitoring of the patient, by the fact that the electrogram is measured and checked at short time intervals. When data telecommunication is employed, moreover, the patient can also be monitored without having to visit a clinic for that purpose.

The measurement and monitoring of the intramyocardial electrogram is subject to some uncertainties, since the measured results can also be modified by other influences, such as the variations of daily rhythm in the electrocardiogram, the exercise status of the patient and the medication. Thus a drop of the measured cardiac voltage signals is not necessarily due in each case to an incipient rejection reaction.

The object of the invention is to provide, for monitoring a patient for rejection reactions to an implanted organ, especially a transplanted heart, a method and apparatus that represents an addition to the known methods and that improves the diagnosis.

The invention is based on the knowledge that functional changes of organs and especially functional changes of the heart are associated with changes of the electrophysiological properties of the tissue, which changes can be detected by a change of the electrical resistance and especially the impedance of the tissue (B. C. Penney et al., Medical & Biological Engineering & Computing, 1985, 23, p. 1–7). It is assumed that these changes are due to interstitial edemas, infiltration in the interstitial tissues and electrophysiological changes of the cell membranes and of their capacitive properties.

SUMMARY OF INVENTION

According to the invention, the occurrence of rejection reactions to an implanted organ, especially to a transplanted heart, is monitored by measurement of the electrical impedance of the tissue of that organ. For this purpose a telemetry measuring unit is implanted in the body of the patient The measuring unit is provided with electrodes that can be implanted in the organ. Via two of these implanted electrodes, the current electrodes, an electrical current is supplied and passed through the tissue of the implanted organ. By means of two implanted electrodes, the measuring electrodes, the impedance (resistance) of the tissue through which the current is flowing is measured or determined computationally from a measured value.

For this purpose it is possible to use merely one single implanted electrode pair, which serves both as the current electrodes for the current supply and as the measuring electrodes for the impedance measurement. In this version, however, effects caused by polarization can occur at the electrodes and impair the measurement accuracy. According to the invention, therefore, two electrode pairs are preferably used, the current being supplied via one electrode pair (the current electrodes) and the other electrode pair (the measuring electrodes) being used for voltage or impedance measurement. In this version, polarization effects at the electrodes have little influence on the measuring accuracy.

Particularly in the use of separate electrode pairs as the current electrodes and measuring electrodes, it is important that the measuring electrodes also be disposed reliably and as constantly as possible in the current path, in order to obtain measured values that are comparable for the diagnosis. If physiological changes in the tissue cause the current flowing between the current electrodes to seek a different path through the tissue, this could lead to the situation that the measuring electrodes are no longer located in the region of the current path or that they are located in a different region of the current path, with the result that falsified measured results are obtained.

In order to preclude such influences as much as possible, the measuring electrodes are disposed according to the invention such that each annularly surrounds one and only one current electrode. By this disposition of the electrodes it is reliably ensured that the current path from the one current electrode to the other current electrode must pass the two measuring electrodes. Thus the two measuring electrodes are located reliably and reproducibly in the current path through the tissue of the organ to be monitored.

Such an electrode configuration can be realized in different ways. The two current electrodes can be disposed next to each other and separate, each current electrode being annularly surrounded by one measuring electrode, or both measuring electrodes can annularly surround the one current electrode concentrically. Moreover, all electrodes can be disposed concentrically nested inside each other, the innermost and the outermost electrodes being the current electrodes and the two measuring electrodes being disposed concentrically in the annular space between the two current electrodes.

In order to permit simple implantation of the electrodes and reliable positioning of the implanted electrodes, the electrodes are preferably inserted in a support element comprising of an electrical insulating material that is well tolerated by the tissue. The support element holds the electrodes in the specified disposition and facilitates the implantation of the electrodes. Expediently, the electrodes project from the support element only with their annularly disposed front ends, and so a precisely defined electrode configuration is obtained.

It is self-evident that the electrodes do not necessarily have to be of circular form, but can also have a different closed form, for example an elliptical form, a rectangular form or the like. It is also evident that the electrodes do not necessarily have to be of fully closed form, but can also be divided into segments, provided the gaps between the individual segments are not so large that a substantial fraction of the current flow can travel through these gaps past the measuring electrodes.

The implantable telemetry measuring unit is equipped with a transmitter-receiver circuit, whereby it can be coupled with a telemetry control unit disposed outside the body of the patient. The coupling is preferably effected via electromagnetic waves with a carrier frequency of, for example, 40 kHz. By means of inductive coupling, for example, on the one hand the measured values of the measuring unit are transmitted to the telemetry control unit and on the other hand the telemetry measuring unit can be turned on and off by the telemetry control unit, via this inductive coupling. Thus the telemetry measuring unit is operated only within specified time intervals, in order to perform the measurement and to transmit the measured values to the control unit. During the other time intervals the telemetry measuring unit is turned off, so that the supply battery of the telemetry measuring unit is drained as little as possible and the longest possible service life is achieved.

The measured values acquired by the telemetry measuring unit and transmitted to the telemetry control unit can be evaluated directly in the control unit, if the control unit is located in a clinic and operated by specialized personnel. Preferably, however, the telemetry control unit is connected via data telecommunication with the clinic and the measured values stored in the telemetry control unit can be called in for evaluation by the clinic via data telecommunication. Thus the measurements for monitoring of rejection reactions that may occur can be performed by the patient at home, preferably during the night time periods of rest. The evaluation of the measurement can be performed later in the clinic at any desired time. Thus monitoring at short time intervals is possible without the need for a time-consuming and expensive visit of the patient to the clinic.

The resistance measurement by the telemetry measuring unit determines the impedance of the body tissue, since the electrophysiological resistance changes associated with the rejection reactions are also manifested in particular as a change in the capacitive property of the tissue. In order to measure the impedance changes and in particular the changes in the capacitive reactance, the current electrodes of the measuring unit are fed with alternating current. Any kind of impedance measurement apparatus known from the prior art is usable. For example, even the phase shift that the capacitive reactance causes in the a.c. voltage signal can be determined.

In a preferred embodiment, the a.c. voltage consists of a square-wave pulse voltage, and the change of pulse form due to the capacitance of the tissue, including in particular the change of steepness of the leading edge of the pulses on the basis of integration, is determined as the measured value.

BRIEF DESCRIPTION OF THE DRAWINGS

The invention will be explained in more detail in the following on the basis of practical examples, which are illustrated in the attached drawing, wherein

FIG. 7 schematically shows a set-up for monitoring a patient.

DESCRIPTION OF THE PREFERRED EMBODIMENTS

Figure 1:
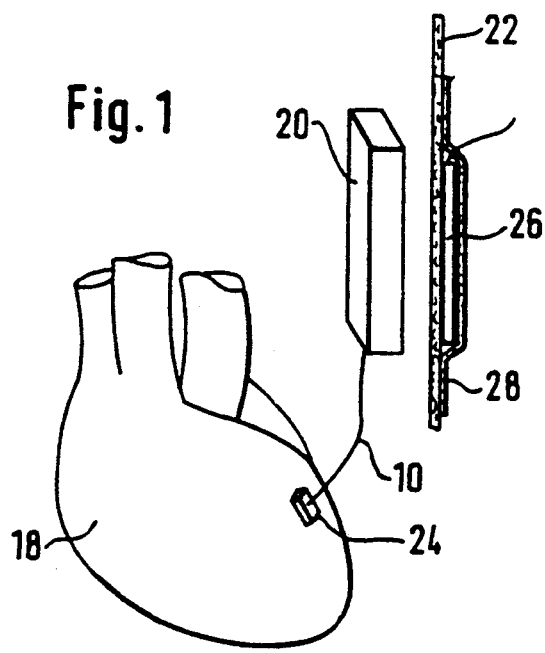
FIG. 1 is a schematic diagram of the apparatus for monitoring a transplanted heart; in accordance with present invention

In the implantation of a donor organ, especially of a donor heart, a telemetry measuring unit 20 is implanted together with the heart 18 in the patient. The measuring unit 20 has a miniaturized, battery-powered electronic circuit for impedance measurement. The measuring unit 20 also has a transmitter-receiver circuit for electromagnetic waves with a carrier frequency of, for example, 40 kHz, one coil being able to function as the antenna. Via the transmitter-receiver circuit the electronic measuring circuit can be controlled by means of signals transmitted inductively from outside through the body surface 22 of the patient into the body interior, in order to start, control and stop measuring-program sequences. Similarly, the measured values acquired by the measuring circuit can be transmitted inductively from the body interior to the outside via the transmitter-receiver circuit.

The telemetry measuring unit 20 is connected via a cable 10 with an electrode configuration 24 implanted in the transplanted heart 18. The electrode configuration 24 has a support element 12, which is cast from an electrically insulating material that is well tolerated by the tissue, for example from silicone rubber, polyurethane or the like. In each case, two electrode pairs are embedded in the support element 12, namely one pair of current electrodes 14 and one pair of measuring electrodes 16. The current electrodes 14 are fed with current by the measuring unit 20, so that an electric current flows from the one current electrode 14 through the tissue of the implanted heart 18 to the other current electrode 14. At the measuring electrodes 16 a voltage is picked up that represents a measure of the impedance of the tissue region which is located between the measuring electrodes 16 and through which the current is flowing. The impedance value is transmitted inductively by the telemetry measuring unit 20 to a receiver coil 26, which is attached externally, by means of an adhesive tape 28, for example, over the implanted telemetry measuring unit 20, on the body surface 22 of the patient. The receiver coil 26 is connected with a telemetry control unit of a bedside patient system, which acquires, processes and stores the measured values and relays them by data telecommunication.

In order to ensure that the current flowing between the current electrodes 14 takes a current path through the body tissue that is always as constant as possible relative to the measuring electrodes 16, the measuring electrodes 16 are disposed relative to the current electrodes 14 such that the measuring electrodes 16 each annularly surround one and only one current electrode 14. Even if the current path between the current electrodes 14 shifts slightly in the tissue, it nevertheless always intersects the measuring electrodes 16, and so reliably usable measured signals suitable for monitoring are obtained.

Figures 2, 3:
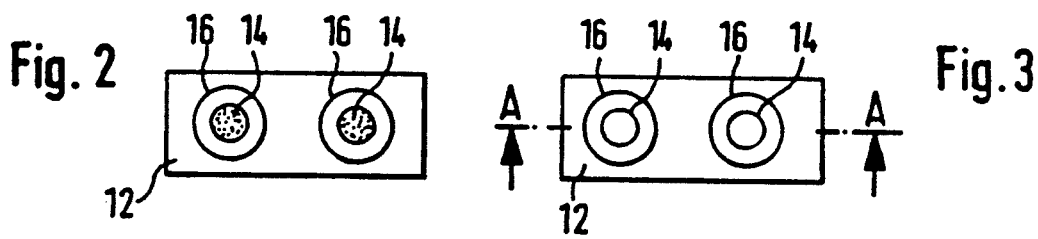
FIG. 2 is a front view of a first embodiment of an electrode configuration according to the invention.
FIG. 3 is a corresponding front view of a second embodiment; thereof
Figure 4:
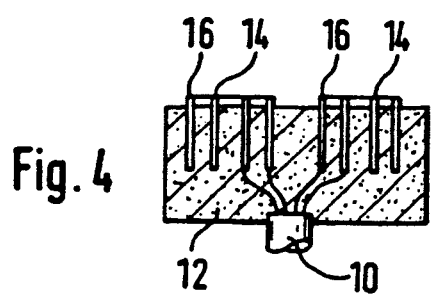
FIG. 4 is a section through the electrode configuration of FIG. 3, along the line A—A.

In the practical examples of FIGS. 2 and 3, two current electrodes 14 are disposed next to each other and separate in the support element 12, each of the two current electrodes 14 being surrounded concentrically by one circular measuring electrode 16. The current electrodes 14 and the measuring electrodes 16 are embedded in the support element 12 in such a way that they project from the surface of the support element 12 only with their front ends, as can be seen in FIG. 4. The regions of the electrodes 14 and 16 coming into contact with the body tissue therefore form rings lying in one plane.

In the practical example of FIG. 2, the internally disposed current electrodes 14 are made as solid rods, whereas in the practical example of FIGS. 3 and 4 they are made as hollow cylinders.

Figures 5, 6:
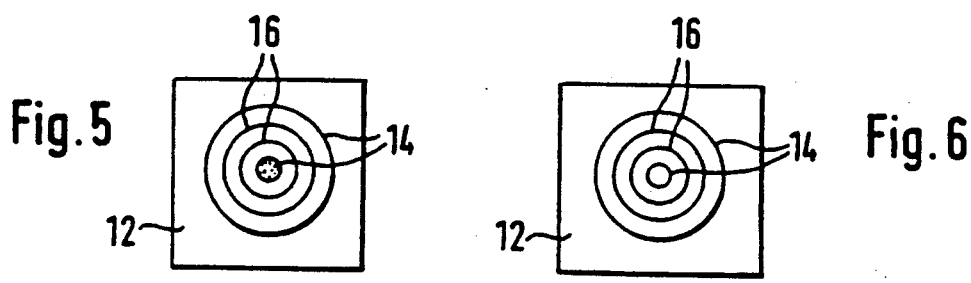
FIG. 5 is a front view of a third embodiment.
FIG. 6 is a front view of a fourth embodiment.

In the practical example of FIGS. 5 and 6, the four electrodes are disposed concentrically nested inside each other. The innermost and the outermost electrodes are the current electrodes, while the two measuring electrodes 16 are disposed concentrically in the annular space between the current electrodes 14. Here also the current electrodes 14 and the measuring electrodes 16 project from the insulating support element 12 only with their front ends, as is shown in corresponding manner in FIG. 4. The regions of the electrodes 14 and 16 coming into electrical contact with the body tissue therefore represent a set of concentric rings.

The practical examples of FIGS. 5 and 6 differ in the fact that the internal current electrode 14 is a solid rod in the practical example of FIG. 5, whereas it is a hollow cylinder in the practical example of FIG. 6.

The electrodes 14 and 16 consist of a metal with good electrical conductivity that is well tolerated by the tissue, such as, for example, gold, silver, platinum, iridium or alloys.

Via the current electrodes 14 an a.c. voltage is applied to the tissue by the measuring circuit. The impedance of the body tissue is determined via the measuring electrodes 16. The impedance consists substantially of an ohmic resistance and a capacitive reactance. The ohmic resistance depends substantially on the extracellular space of the tissue, whereas the capacitive reactance depends substantially on the properties of the cell membrane. As a result of ischemia of the tissue during a rejection reaction, an intracellular edema with simultaneous shrinkage of the extracellular space occurs. Thereby both the ohmic resistance and the capacitive reactance are changed and thus the impedance of the tissue is changed.

Preferably a square-wave pulse voltage is used as the a.c. voltage. The change of the pulse form is a measure of the impedance. The change of the pulse height corresponds substantially to the ohmic resistance, whereas the change of the steepness of the leading edges of the square-wave pulses is substantially a measure of the capacitive reactance.

To monitor for possible rejection reactions, the receiver coil 26 of the telemetry control unit is disposed by the patient, preferably during the night rest periods, on the body surface 22 over the implanted telemetry measuring unit 20. The control unit transmits the ON signal via the receiver coil 26 to the measuring unit 20. The measuring unit 20 transmits the measured values for a predetermined measuring duration via the inductive coupling to the control unit. The measured values are stored in the bedside system and can be called in by the clinic by means of a modem via a telephone line and evaluated in the electrophysiological laboratory of the clinic. This monitoring and evaluating system is schematically represented in FIG. 7.

The invention is intended in particular for monitoring an implanted heart. However, it is also suitable for monitoring other implanted organs, such as, for example, for monitoring a liver, kidney, pancreas, lung and the like.

I claim:

1. A method for monitoring a patient for rejection reactions to a transplanted heart, comprising:
    coupling a telemetry measuring unit implanted in the body of a patient with a telemetry control unit disposed outside the body,
    controllably passing an electric current from the telemetry measuring unit through the tissue of the organ via electrodes implanted in the organ,
    measuring the electrical impedance and transmitting a signal representative thereof to the telemetry control units, and
    monitoring said signal to determine the presence or absence of rejection reactions.

2. A method according to claim 1, wherein the current is supplied and the impedance is measured by the same electrodes.

3. A method according to claim 1, wherein the current is supplied by two electrodes and the impedance is measured by two additional electrodes.

4. A method according to claim 1, wherein an alternating current is supplied to the electrodes, and the phase shift caused by capacitive reactance is measured.

5. A method according to claim 1, wherein a square-wave pulse current is supplied to the electrodes, and the change of the pulse form is measured.

6. A method according to claim 5, wherein the height and the steepness of the leading edges of the pulses is measured.

* * * * *